(12) United States Patent
Nagashima et al.

(10) Patent No.: US 7,272,439 B2
(45) Date of Patent: Sep. 18, 2007

(54) WORKING ELECTRODE ASSEMBLY FOR IONTOPHORESIS AND IONTOPHORESIS DEVICE

(75) Inventors: Masumi Nagashima, Shunan (JP); Kenji Fukuta, Shunan (JP); Kanji Sakata, Shunan (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 11/253,749

(22) Filed: Oct. 20, 2005

(65) Prior Publication Data

US 2006/0089591 A1    Apr. 27, 2006

(30) Foreign Application Priority Data

Oct. 21, 2004    (DE)    ............... 2004-307353

(51) Int. Cl.
   *A61N 1/30*    (2006.01)
(52) U.S. Cl. ..................................... 604/20
(58) Field of Classification Search ............ 604/892.1, 604/20, 500, 290, 21, 890.1; 424/447, 449; 607/149, 152
   See application file for complete search history.

(56) References Cited

U.S. PATENT DOCUMENTS

| | | | |
|---|---|---|---|
| 4,722,726 A * | 2/1988 | Sanderson et al. | 604/20 |
| 4,731,049 A * | 3/1988 | Parsi | 604/20 |
| 5,169,383 A * | 12/1992 | Gyory et al. | 604/20 |
| 5,302,269 A * | 4/1994 | Eisman et al. | 204/252 |
| 5,496,266 A * | 3/1996 | Haak et al. | 604/20 |
| 5,894,021 A | 4/1999 | Okabe et al. | |
| 2004/0138609 A1* | 7/2004 | Fukuta et al. | 604/20 |

FOREIGN PATENT DOCUMENTS

| | | |
|---|---|---|
| EP | 1 602 366 A1 | 12/2005 |
| JP | 63-502404 A | 9/1988 |
| JP | 3-504813 A | 10/1991 |
| JP | 4-297277 A | 10/1992 |
| JP | 2000-229128 A | 8/2000 |
| JP | 2000-229129 A | 8/2000 |
| JP | 2000-237328 A | 9/2000 |
| JP | 2000-237329 A | 9/2000 |
| JP | 2004-188188 A | 7/2004 |
| JP | 2004-202057 A | 7/2004 |
| WO | WO-87/04936 A1 | 8/1987 |
| WO | WO-90/04432 A1 | 5/1990 |

\* cited by examiner

*Primary Examiner*—Nicholas D. Lucchesi
*Assistant Examiner*—Christopher D. Koharski
(74) *Attorney, Agent, or Firm*—Birch, Stewart, Kolasch & Birch, LLP (57) ABSTRACT

A working electrode assembly for iontophoresis having a working electrode, a medicine-containing portion containing an ionic medicine, and an ion-exchange membrane arranged between the working electrode and the medicine-containing portion, wherein said ion-exchange membrane has both the anion-exchange groups and the cation-exchange groups, and between these anion-exchange groups and cation-exchange groups, the ion-exchange groups of the one side are contained in an excess amount compared to the other ion-exchange groups. The working electrode assembly effectively prevents the contact between the medicine and the working electrode and, at the same time, accomplishes a high efficiency for administering the medicine.

4 Claims, 1 Drawing Sheet

WORKING ELECTRODE ASSEMBLY FOR IONTOPHORESIS AND IONTOPHORESIS DEVICE

CROSS-REFERENCE TO RELATED APPLICATIONS

The present application claims priority under 35 U.S.C. § 119 to Japanese Patent Application No. 2004-307353, filed on Oct. 21, 2004.

BACKGROUND OF THE INVENTION

1. Field of the Invention

The present invention relates to a working electrode assembly used for the iontophoresis (ionic permeation therapy) for permeating, into the living body, an ionic medicine useful for the living body by utilizing the electrophoresis and to an iontophoresis device.

2. Description of the Related Art

The iontophoresis for permeating, into the living body, an ionic medicine useful for the living body by utilizing the electrophoresis is also called ionic permeation therapy or ion introduction method, and has been widely known as a method of administering a medicine of a required amount into a diseased part in a pain-free state.

In the iontophoresis, so far, a medicine-containing layer impregnated with an ionic medicine is placed on the living body, a working electrode is arranged on the side opposite to the living body with the medicine-containing layer sandwiched therebetween, a counter electrode is placed on the living body separated away from the medicine-containing layer, and an electric current is flown across the working electrode and the counter electrode from a power source causing the ionic medicine to permeate into the living body.

The iontophoresis is, usually, carried out by using a working electrode assembly which incorporates a working electrode and a medicine-containing layer containing an ionic medicine accompanied, however, by such inconvenience that a solvent such as water (used for dissolving the ionic medicine) is electrolyzed on the surface of the electrode causing the pH to vary or the ionic medicine which is in contact with the electrode is decomposed. To prevent the above inconvenience, therefore, there has been proposed a technology of arranging an ion-exchange membrane between the working electrode and the medicine-containing layer (see, for example, patent documents 1 to 5 described below).

That is, a voltage applied across the working electrode and the counter electrode accelerates the electrolysis of water, whereby the pH of the medicine-containing aqueous solution varies due to $H^+$ ions and $OH^-$ ions that are formed causing the living body to be inflamed, the medicine that has come in direct contact with the electrode to be consumed upon reacting (decomposed) on the electrode surface and, besides, often forming compounds that may adversely affect the living body. According to the technologies proposed in the above patent documents 1 to 5, therefore, an ion-exchange membrane of the type that permits the passage of ions of a polarity opposite to that of the pharmacological ions of the ionic medicine is arranged between the working electrode and the medicine-containing layer to prevent the decomposition of the medicine and to prevent the $H^+$ ions or the $OH^-$ ions formed on the electrode from migrating to the side of the medicine-containing layer.

When the ion-exchange membrane which permits the passage of ions of a polarity opposite to that of the pharmacological ions is provided between the working electrode and the medicine-containing layer, however, the ion-exchange membrane must have an increased thickness to reliably prevent the pharmacological ions from migrating to the side of the working electrode. However, an increase in the thickness of the membrane results in an increase in the electric resistance (membrane resistance) of the ion-exchange membrane and in a decrease in the energy efficiency and in the efficiency for administering the medicine.

In the iontophoresis, further, there has been proposed a technology for arranging a pharmacological ion-permeating ion-exchange membrane between the medicine-containing layer and the living body (see, for example, patent documents 3 to 5). That is, upon providing an ion-exchange membrane of the type that permits the passage of ions of the same polarity as that of the pharmacological ions of the ionic medicine, it is attempted to prevent sodium cations, potassium cations and chloride anions from migrating to the side of the working electrode assembly from the side of the living body in order to improve the efficiency for administering the medicine.

In recent years, further, study has been vigorously forwarded concerning the iontophoresis device of the portable type for carrying out the iontophoresis at any time and on any place. The portable iontophoresis device of this type uses cells such as button cells as a power source, and it becomes important to maintain a high medicine administering efficiency when a voltage value remains constant (constant voltage).

Patent document 1: JP-T-63-502404
Patent document 2: JP-T-3-504813
Patent document 3: JP-A-4-297277
Patent document 4: JP-A-2004-188188
Patent document 5: JP-A-2004-202057

SUMMARY OF THE INVENTION

It is, therefore, an object of the present invention to provide a working electrode assembly for iontophoresis, which is capable of effectively preventing the pharmacological ions from migrating to the side of the working electrode and, at the same time, maintaining a high efficiency for administering a medicine to the living body.

Another object of the present invention is to provide a working electrode assembly for iontophoresis, which is capable of maintaining a high efficiency for administering the medicine even when a constant voltage (voltage value remains constant) is applied across the electrodes by using cells such as button cells.

A further object of the present invention is to provide an iontophoresis device equipped with the above-mentioned working electrode assembly.

The present inventors have conducted a keen study in an effort to improve the efficiency for administering a desired medicine in the iontophoresis by using an ion-exchange membrane between the electrode (working electrode) and the medicine-containing portion. As a result, the inventors have discovered that the medicine can be effectively prevented from migrating to the side of the working electrode and, at the same time, a high efficiency for administering the medicine is maintained by selectively using the ion-exchange membrane of predetermined character, and have finished the present invention.

That is, according to the present invention, there is provided a working electrode assembly for iontophoresis having a working electrode, a medicine-containing portion containing an ionic medicine, and an ion-exchange membrane arranged between the working electrode and the medicine-containing portion, wherein said ion-exchange membrane has both the anion-exchange groups and the cation-exchange groups, and between these anion-exchange groups and cation-exchange groups, the ion-exchange groups of the one side are contained in an excess amount compared to the other ion-exchange groups.

Preferably, the above ion-exchange membrane is formed by using, for example, a porous film as a reinforcement, and filling voids in the porous film with a crosslinking ion-exchange resin.

According to the present invention, there is further provided an iontophoresis device comprising the working electrode assembly, a counter electrode assembly having a counter electrode facing the working electrode, and a power source unit electrically connected to the working electrode assembly and to the counter electrode assembly, for permeating, into the living body, an ionic medicine contained in the medicine-containing portion of the working electrode assembly relying upon the electrophoresis.

According to the present invention, the ion-exchange membrane having the above-mentioned characteristics is arranged between the working electrode and the medicine-containing portion, making it possible to effectively prevent the contact between the medicine and the working electrode as well as to achieve a high efficiency for administering the medicine. In particular, the ion-exchange membrane used in the present invention, has both the anion-exchange groups and the cation-exchange groups, and between these anion-exchange groups and cation-exchange groups, the ion-exchange groups of the one side are contained in an excess amount compared to the other ion-exchange groups, making it possible to greatly decrease the migration of medicine to the side of the working electrode and to greatly suppress the decomposition of medicine while maintaining a high efficiency for administering the medicine without decreasing the efficiency for administering the medicine as demonstrated in Examples appearing later.

The present invention is a very useful technology capable of greatly suppressing the decomposition of medicine and achieving a high efficiency for administering the medicine even when a constant voltage is applied across the electrodes by using, particularly, cells such as button cells.

DETAILED DESCRIPTION OF THE INVENTION

A working electrode assembly for iontophoresis of the present invention is used for an iontophoresis device in combination with a counter electrode assembly that has a counter electrode facing the working electrode, and works to administer, to the living body, an ionic medicine, usually, through an ion-exchange membrane by utilizing the electrophoresis.

(Working Electrode Assembly 1)

Figure 1:
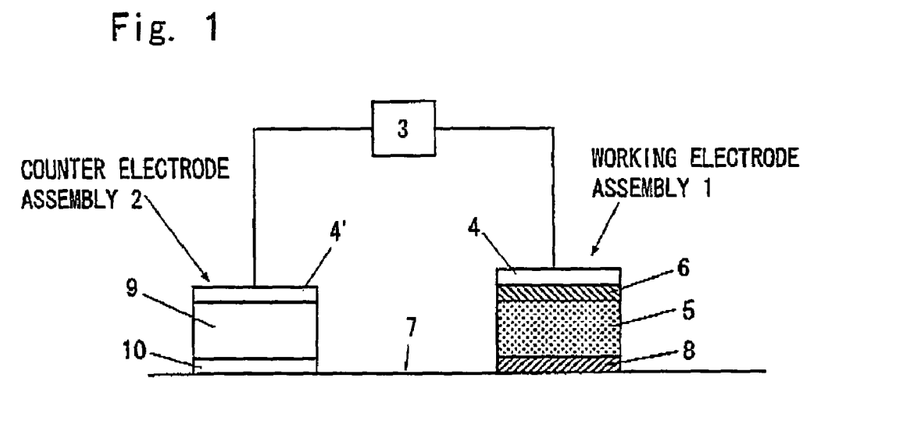
FIG. 1 is a view schematically illustrating a representative constitution of an iontophoresis device using a working electrode assembly of the present invention.

The working electrode assembly 1 includes a working electrode 4 and a medicine-containing portion 5 containing an ionic medicine. A medicine-blocking ion-exchange membrane 6 is arranged between the working electrode 4 and the medicine-containing portion 5. As required, further, a medicine-permeating ion-exchange membrane 8 is provided so as to be opposed to the medicine-blocking ion-exchange membrane with the medicine-containing portion 5 sandwiched therebetween. In the working electrode assembly 1 as shown in FIG. 1, there are arranged the working electrode 4, medicine-blocking ion-exchange membrane 6, medicine-containing portion 5 and medicine-permeating ion-exchange membrane 8 in this order, the medicine-permeating ion-exchange membrane 8 facing the living body interface (skin) 7 to where the medicine is to be administered. Usually, these members are laminated in a backing material (not shown) to constitute the working electrode assembly 1.

As required, further, an ion-permeating sheet made of an ionically conducting gel, a porous film or a woven fabric may be provided between the medicine-permeating ion-exchange membrane 8 and the living body interface 7. The gel or the sheet may assume a structure integral with the working electrode assembly 1. Or, the gel or the sheet may be held relative to the living body interface 7 only during the use. Though not illustrated, the working electrode assembly 1 may further include an ionically conducting gel, an ionically electrolytic solution, or a porous film or a woven fabric impregnated with the ionically electrolytic solution between the working electrode 4 and the ion-exchange membrane 6.

-Working Electrode 4-

As the working electrode 4 in the working electrode assembly 1, there can be used, without limitation, any electrode that is usually used in the electrochemical processes. For example, there can be used an electrode made of an electronically conducting material such as gold, platinum, silver, copper, nickel, zinc or carbon, or a self-sacrificing electrode such as semiconductor electrode or silver/silver chloride, which may be used alone or in combination. Preferably, there can be exemplified gold, platinum, silver and carbon. These electrodes may be plates, sheets, meshes or an amorphous laminate of fibers, which is shaped and worked like a paper, or may be the one obtained by plating or vaporizing an electrode member on the ion-exchange membrane 6.

-Medicine-Containing Portion 5-

As the medicine-containing portion 5 in the working electrode assembly 1, there can be used, without any limitation, a medicine-containing layer that is used in the ordinary iontophoresis. That is, there can be used a solution obtained by dissolving an ionic medicine in a solvent such as water or ethanol, a gel obtained by mixing the above solution with a polyvinyl alcohol or a polyvinyl pyrrolidone, or the one obtained by impregnating a porous film or a gauze with the above solution. There is no particular limitation on the ionic medicine contained in the medicine-containing portion 5. The ionic medicine may be any substance that comprises cations and anions and exhibits pharmacological effect as the cations or anions enter into the living body.

Examples of the ionic medicine of which the cations exhibit the effect (hereinafter often referred to as cationic medicine) include anesthetics such as procaine hydrochloride, lidocaine hydrochloride and dibucaine hydrochloride; anti-malignant tumor agents such as mitomycin and pleomycin hydrochloride; anodynes such as morphine hydrochloride; steroids such as medroxyprogesterone acetate;

histamine and insulin. As the ionic medicine of which the anions exhibit the effect (hereinafter often referred to as anionic medicine), there can be exemplified vitamin compounds such as vitamin B2, vitamin B12, vitamin C, vitamin E and folic acid; anti-inflammatory agents such as aspirin and ibuprofen; adrenocortical hormones such as dexamethasone-type water-soluble compounds; and antibiotics such as benzylpenicillin potassium. Among them, when the ionic medicine having the formula weight of pharmacological ions in a range of 300 to 1500 and, particularly, 400 to 1000 is used, the iontophoresis device of the present invention exhibits an efficiency of administration higher than those of the conventional devices.

-Ion-Exchange Membrane 6-

In the present invention, there is used the medicine-blocking ion-exchange membrane 6 (hereinafter often called dipolar ion-exchange membranes) which has both anion-exchange groups and cation-exchange groups, but contains either the anion-exchange groups or the cation-exchange groups in an excess amount compared to the other ion-exchange groups. That is, when the cationic medicine is used, the dipolar ion-exchange membrane (anion-exchange membrane) has both the anion-exchange groups and the cation-exchange groups, and contains the anion-exchange groups in an excess amount. This dipolar ion-exchange membrane permits the anions to pass through but blocks the cations. When the anionic medicine is used, the dipolar ion-exchange membrane has both the anion-exchange groups and the cation-exchange groups, and contains the cation-exchange groups in an excess amount. This dipolar ion-exchange membrane permits the cations to pass through but blocks the anions. Generally, such ion-exchange membrane 6 (dipolar ion-exchange membrane) has a membrane resistance of not larger than $0.45 \ \Omega \cdot cm^2$ in a 3 mol/L sulfuric acid aqueous solution, and a permeation factor for the ionic medicine of not larger than $0.001 \ \mu mols/hr \cdot cm^2$ as measured at a current density of $0.5 \ mA/cm^2$. By using the dipolar ion-exchange membrane as the ion-exchange membrane 6, the medicine permeation factor can be greatly decreased, the medicine can be reliably prevented from decomposing on the surface of the working electrode 4 and the efficiency for administering the medicine can be enhanced as compared with those of when the monopolar ion-exchange membrane is used even when the membrane has a small thickness (low membrane resistance) without decreasing the energy efficiency of the iontophoresis device as a whole as demonstrated in Examples appearing later.

The anion-exchange groups or the cation-exchange groups possessed by the dipolar ion-exchange membrane may be either groups known as the ion-exchange groups of the ion-exchange resin. Concrete examples of the ion-exchange groups are, in the case of anion-exchange groups, primary to tertiary amino groups, quaternary ammonium groups, pyridyl groups, imidazole groups, quaternary pyridinium groups and quaternary imidazolium groups. In the case of cation-exchange groups, examples of the ion-exchange groups are sulfonic acid groups, carboxylic acid groups, phosphoric acid groups, and phosphonic acid groups.

In the present invention, the ion-exchange membrane 6 (dipolar ion-exchange membrane) has a thickness in a range of, usually, 5 to 150 μm, preferably, 10 to 120 μm and, particularly preferably, 15 to 60 μm in relation to the membrane resistance and the medicine permeation factor that are lying in the above-mentioned ranges. This is because, the membrane resistance, generally, decreases with a decrease in the thickness of the ion-exchange membrane, and the medicine permeation factor increases.

In the present invention, the dipolar ion-exchange membrane exhibits a decreased medicine permeation factor when the amounts of the two ion-exchange groups are close to each other and exhibits a decreased membrane resistance when the amount of the ion-exchange groups excessively existing is great (when there is a difference in the amount between the two ion-exchange groups). It is therefore desired that the amount of the ion-exchange groups of a polarity excessively existing is 1.01 to 10 times, particularly, 1.05 to 5 times and, most desirably, about 1.1 to about 3 times as great as the amount of the other ion-exchange groups. The amount of the ion-exchange groups in the membrane can be determined by the spectral analysis such as infrared spectrophotometry or by the elemental analysis.

To further lower the membrane resistance, it is desired that the amount of the ion-exchange groups is great in the ion-exchange membrane as described above. It is therefore desired that the amount of the ion-exchange groups excessively existing is not smaller than 0.1 mmol per gram of the dry membrane, more desirably, not smaller than 0.2 mmols per gram of the dry membrane and, particularly, not smaller than 0.5 mmols per gram of the dry membrane. There is no upper limit on the amount of the ion-exchange groups of a polarity excessively existing. However, it becomes difficult to produce the ion-exchange membrane when it contains the ion-exchange groups in too large amounts. Even if such an ion-exchange membrane is forcibly produced, the mechanical strength often decreases. It is therefore desired that the amount of the ion-exchange groups is not larger than 5 mmols per gram of the dry membrane, preferably, not larger than 4 mmols per gram of the dry membrane and, particularly preferably, not larger than 3 mmols per gram of the dry membrane.

Though the ion-exchange groups of the excess side are contained in the above-mentioned amount in the dipolar ion-exchange membrane that contains the two kinds of ion-exchange groups, part of the ion-exchange groups forms ion complexes with the other ion-exchange groups. Therefore, the ion-exchange capacity measured by a predetermined method becomes smaller than the amount of the ion-exchange groups of the excess side and, hence, becomes, usually, 0.1 to 3.0 mmols per gram of the dry membrane, and, further, 0.1 to 2 mmols per gram of the dry membrane and, particularly, 0.3 to 1.5 mmols per gram of the dry membrane.

In the present invention, the ion-exchange membrane 6 (dipolar ion-exchange membrane) is preferably formed by using, for example, a porous film as a reinforcement, and filling the voids in the porous film with a crosslinking ion-exchange resin from the standpoint of excellent strength and small probability of breakage. For example, with the ion-exchange membrane using the woven fabric as a reinforcement or with the ion-exchange membrane produced by the casting method, that have heretofore been known, it is difficult to set both the membrane resistance and the medicine permeation factor to lie within the above-mentioned ranges.

It is desired that the thickness of the porous film is, preferably, 5 to 140 μm, more preferably, 10 to 120 μm and, most preferably, 15 to 55 μm so that the ion-exchange membrane will assume the above-mentioned thickness. Usually, the thickness of the ion-exchange membrane produced by the production method that will be described later is nearly equal to the thickness of the porous film used as the reinforcement plus 0 to 20 μm. When the porous film is too thick, the obtained ion-exchange membrane exhibits a too high electric resistance, which is not desirable. When its thickness is too small, on the other hand, the medicine permeation factor tends to become too great.

It is further necessary that the porous film has pores penetrating through from the front surface up to the back surface. From the standpoint of obtaining the ion-exchange membrane having a small thickness, an excellent strength and a small electric resistance, it is desired that the average pore size is 0.005 to 5.0 µm and, particularly, 0.01 to 2.0 µm and that the percentage of voids is 20 to 95% and, particularly, 30 to 90%. It becomes easy to produce the ion-exchange membrane having a low electric resistance as the average pore size increases or as the percentage of voids increases. When the pore size or the percentage of voids increases too much, however, the mechanical strength decreases and the membrane cannot be used with ease. The average pore size stands for an average diameter measured in compliance with a bubble point method (JIS K 3832-1990).

It is further desired that the material of the porous film is a thermoplastic resin. As the thermoplastic resin, there can be used without limitation polyolefin resins such as homopolymers or copolymers of α-olefins like ethylene, propylene, 1-butene, 1-pentene, 1-hexene, 3-methyl-1-butene, 4-methyl-1-pentene, and 5-methyl-1-heptene; vinyl chloride resins such as polyvinyl chloride, vinyl chloride/vinyl acetate copolymer, vinyl chloride/vinylidene chloride copolymer, and vinyl chloride/olefin copolymer; fluorine-contained resins such as polytetrafluoroethylene, polychlorotrifluoroethylene, vinylidene polyfluoride, tetrafluoroethylene/hexafluorbpropylene copolymer, tetrafluoroethylene/perfluoroalkylvinyl ether copolymer and tetrafluoroethylene/ethylene copolymer; polyamides such as nylon 6 and nylon 66; and polyimide resin. It is, however, desired to use a polyolefin resin from the standpoint of mechanical strength, chemical stability, resistance against the chemicals, and compatibility with the ion-exchange resin. As the polyolefin resin, it is particularly preferred to use a polyethylene and a polypropylene, and it is most desired to use the polyethylene.

The porous film can be easily obtained by molding a resin composition comprising a thermoplastic resin composition and an organic liquid into a sheet or a film and, then, extracting the organic liquid therefrom by using a solvent. Or, the porous film can be further easily prepared by stretching a sheet filled with an inorganic filler and/or an organic filler. Further, many porous films have been placed in the market. Usually, therefore, the porous films placed in the market may be used.

The ion-exchange membrane 6 (dipolar ion-exchange membrane) can be produced by filling the voids in the porous film with the crosslinking ion-exchange resin into which have been introduced both the anion-exchange groups and the cation-exchange groups in amounts of a predetermined ratio. A representative method will now be described below.

A first method comprises preparing a crosslinking polymerizable composition, which contains a polymerizable monomer having either the anion-exchange groups or the cation-exchange groups, filling the composition into the voids in the porous film followed by polymerization to produce an ion-exchange membrane (hereinafter called a precursor membrane) having either the anion-exchange groups or the cation-exchange groups, and infiltrating the polymerizable monomer having ion-exchange groups of an opposite polarity into the precursor membrane, followed by polymerization. When, for example, the precursor having the cation-exchange groups is prepared, a polymerizable monomer having the anion-exchange groups is infiltrated into the precursor membrane, followed by polymerization to obtain a dipolar ion-exchange membrane having the cation-exchange groups and the anion-exchange groups in amounts at a predetermined ratio.

In the first method, the precursor membrane may be produced by using a crosslinking polymerizable composition, which contains a polymerizable monomer having functional groups capable of introducing the anion-exchange groups or the cation-exchange groups, filling the crosslinking polymerizable composition into the voids in the porous film, and after polymerization, introducing the anion-exchange groups or the cation-exchange groups.

According to the second method in contrast with the above first method, the dipolar ion-exchange membrane is produced by using a crosslinking polymerizable composition containing a polymerizable monomer having either the anion-exchange groups or the cation-exchange groups and a polymerizable monomer having functional groups capable of introducing the other ion-exchange groups, infiltrating the crosslinking polymerizable composition into the voids in the porous film, polymerizing the composition to form a precursor membrane, and introducing the other ion-exchange groups to the functional groups of the precursor membrane.

In the first and second methods, when the obtained ion-exchange resin has not been crosslinked as a result of not using the crosslinking agent, it is very difficult to set the medicine permeation factor to be smaller than the above-mentioned value. The crosslinking agent is not necessary when the polymerizable monomer having ion-exchange groups or the polymerizable monomer having functional groups capable of introducing the ion-exchange groups, forms a crosslinking polymer by itself.

As the polymerizable monomer having the above ion-exchange groups or as the polymerizable monomer having functional groups capable of introducing the ion-exchange groups, there can be exemplified the following compounds.
Polymerizable monomers having cation-exchange groups:
  Sulfonic acid type monomers such as styrenesulfonic acid, vinylsulfonic acid, α-halogenated vinylsulfonic acid, 2-(meth)acrylamido-2-methylpropanesulfonic acid, 3-sulfopropane (meth)acrylate, 10-sulfodecane (meth)acrylate and salts corresponding thereto;
  carboxylic acid type monomers such as methacrylic acid, acrylic acid, maleic anhydride, 2-(meth)acryloylethylphthalic acid, 2-(meth)acryloylethylsuccinic acid, 2-(meth)acryloylethylmaleic acid, 2-(meth)acryloylethyl-2-hydroxyethylphthalic acid, 11-(meth) acryloyloxydecyl-1,1-dicarboxylic acid, 4-(meth)acryloyloxyethyltrimellitic acid and salts corresponding thereto; and
  phosphoric acid type monomers such as vinylphosphoric acid, 2-(meth)acryloyloxyethyldihydrogen phosphate, 2-(meth)acryloyloxyethylphenylhydrogen phosphate, 10-(meth)acryloyloxydecyldihydrogen phosphate, 6-(meth)acryloyloxyhexyldihydrogen phosphate, 2-(meth)acryloyloxyethyl 2-bromoethylhydrogen phosphate and salts corresponding thereto.
Polymerizable monomers having anion-exchange groups:
  Amine type monomers such as vinylbenzyltrimethylamine, vinylbenzyltriethylamine, N,N-dimethylaminoethyl (meth) acrylate, N,N-diethylaminoethyl(meth) acrylate, N,N-dimethylaminoethyl(meth) acrylate•methyl chloride salt and N,N-diethylaminoethyl(meth)acrylate•methyl chloride salt;

nitrogen-containing heterocyclic monomers such as vinyl pyridine and vinyl imidazole;

Polymerizable monomers having functional groups capable of introducing ion-exchange groups:

aromatic vinyl compounds such as styrene, α-methylstyrene, 3-methylstyrene, 4-methylstyrene, 2,4-dimethylstyrene, p-tert-butylstyrene, α-halogenated styrene, vinyl naphthalene, chloromethylstyrene, vinylpyridine, and vinylimidazole.

As the crosslinking agent compounded to the crosslinking polymerizable composition, there can be used bifunctional or more highly functional polymerizable monomers such as polyfunctional vinyl compounds like divinylbenzene, divinylsulfone, butadiene, chloroprene, divinylbiphenyl and trivinylbenzene, as well as polyfunctional methacrylic acid derivatives such as trimethylolmethanetrimethacrylic acid ester, methylenebisacrylamide and hexamethylenedimethacrylamide.

In order to adjust properties such as mechanical strength and polymerization property, further, there may be compounded, as required, other monofunctional polymerizable monomers such as acrylonitrile, acrolein and methyl vinyl ketone together with the above-mentioned polymerizable monomers.

Besides, a polymerization initiator may be compounded to the crosslinking polymerizable composition. The polymerization initiator can be used any compound capable of polymerizing the above polymerizable monomers without limitation. Preferably, there can be used organic peroxides capable of effecting the thermal polymerization, such as octanoyl peroxide, lauroyl peroxide, t-butylperoxy-2-ethyl hexanoate, benzoyl peroxide, t-butylperoxyisobutylate, t-butylperoxylaurate, t-hexylperoxybenzoate, and di-t-butyl peroxide.

The polymerizable monomers having the ion-exchange groups, polymerizable-monomers having functional groups capable of introducing ion-exchange groups, crosslinking agents and polymerization initiators may be used in a plurality of kinds in combination. It is further allowable to use the polymerizable monomer having ion-exchange groups in combination with the polymerizable monomer having functional groups capable of introducing the ion-exchange groups.

The crosslinking polymerizable composition blended with polymerizable components such as the above-mentioned polymerizable monomers may, further, be blended with a plasticizer, as required. As the plasticizer, there can be used dibutyl phthalate, dioctyl phthalate, dimethyl isophthalate, dibutyl adipate, triethyl citrate, acetyltributyl citrate or dibutyl sebacate. Further, the crosslinking polymerizable composition may be blended with known additives that have been used for the production of ion-exchange membranes.

In order for the obtained dipolar ion-exchange membrane to possess the membrane resistance and the medicine permeation factor within the above-mentioned ranges in the above crosslinking polymerizable composition, it is desired that the crosslinking agent is blended in an amount of 0.1 to 30 mols and, particularly, about 1 to about 15 mols per a total of 100 mols of the polymerizable monomer having ion-exchange groups, polymerizable monomer having functional groups capable of introducing ion-exchange groups and monofunctional polymerizable monomer used as an arbitrary component. When the degree of crosslinking is too low, the medicine permeation factor becomes too high. When the degree of crosslinking is too high, on the other hand, the membrane resistance tends to become too great.

It is desired that the polymerization initiator is blended in an amount of 0.1 to 20 parts by weight and, preferably, 0.5 to 10 parts by weight per 100 parts by weight of the whole polymerizable monomers that are blended.

There is no particular limitation on the method of bringing the porous film into contact with the crosslinking polymerizable composition. For example, the crosslinking polymerizable composition may be applied onto the porous film, sprayed thereon, or the porous film may be immersed in the crosslinking polymerizable composition. In applying the crosslinking polymerizable composition, there may be employed a method of bringing the two into contact under a reduced pressure so that the voids in the porous film are favorably filled with the composition or a method of pressurized treatment after the contact. When the porous film is to be immersed in the crosslinking polymerizable composition, further, the immersion time is, usually, 0.1 second to ten and several minutes though it may vary depending upon the kind of the porous film or the crosslinking polymerizable composition.

The crosslinking polymerizable composition filled in the porous film that serves as a reinforcement is, usually, thermally polymerized by using an organic peroxide as a polymerization initiator from the standpoint of easy operation and conducting the polymerization relatively homogeneously. To prevent the polymerization from being hindered by oxygen and to maintain smoothness on the surfaces of the membrane, the crosslinking polymerizing composition is, preferably, polymerized under the application of pressure while holding it between polyester films and raising the temperature from normal temperature. The polymerizing conditions may be suitably determined depending upon the kind of the polymerization initiator that is used and the monomer composition, but, usually, consist of a temperature of 50 to 150° C. and, particularly, about 60 to about 120° C. for about 10 minutes to about 10 hours.

In the first method, it is desired that the polymerizable monomer which is for introducing the ion-exchange groups of the opposite polarity to the precursor membrane is used in the form of a crosslinking polymerizable composition blended with a crosslinking agent and a polymerization initiator like in the case of preparing the precursor membrane, and that the crosslinking polymerizable composition is infiltrated into the precursor membrane to conduct the polymerization. The infiltration into the precursor membrane is conducted by such means as immersion. Prior to infiltrating the polymerizable monomer having ion-exchange groups of the opposite polarity (crosslinking polymerizable composition) into the precursor membrane, it is desired that the precursor membrane has been dried so that a quick introduction can be accomplished.

Further, a solvent can be used to infiltrate the crosslinking polymerizable composition into the precursor membrane. It is desired to use a solvent particularly when the polymerizable monomer having ion-exchange groups of the opposite polarity is a solid. There is no particular limitation on the solvent provided it is capable of homogeneously dissolving and dispersing the components in the crosslinking polymerizable composition. Concrete examples include alcohols such as water, methanol, ethanol, 1-butanol and 2-ethoxyethanol; aliphatic hydrocarbons such as hexane, cyclohexane, heptane and 1-octane; aromatic hydrocarbons such as toluene, xylene and naphthalene; ketones such as acetone, cyclohexanone and methyl ethyl ketone; ethers such as dibenzyl ether and diethylene glycol dimethyl ether; halogenated hydrocarbons such as methylene chloride, chloroform and ethylene bromide; alcohol esters of aromatic acids and aliphatic acids, such as dimethyl phthalate, dioctyl phthalate, dimethyl isophthalate, dibutyl adipate, triethyl citrate, acetyltributyl citrate and dibutyl sebacate; and alkylphosphoric esters. As required, these solvents may be used in plural kinds in combination. The solvent is used, usually, in an amount of not larger than 10000 mass times, preferably, not larger than 5000 mass times and, more preferably, not larger than 3000 mass times per 100 parts by mass of the polymerizable monomer having ion-exchange groups of the opposite polarity.

So far as the polymer in the precursor membrane has a crosslinking structure, the dipolar ion-exchange membrane obtained by the first method serves as an ion-exchange membrane of a polarity same as the polarity of the precursor membrane irrespective of the amount of the polymerizable monomer having ion-exchange membrane of the opposite polarity that is used. That is, when the precursor membrane is a cation-exchange membrane, the obtained dipolar ion-exchange membrane serves as a cation-exchange membrane having the cation-exchange groups in an excess amount. When the precursor membrane is an anion-exchange membrane, the obtained dipolar ion-exchange membrane serves as an anion-exchange membrane having the anion-exchange groups in an excess amount.

In the first method, the precursor membrane into which the polymerizable monomer having ion-exchange groups of the opposite polarity has been infiltrated may be polymerized under the same conditions as those of when the precursor membrane is prepared. In particular, it is desired to lightly wipe the surfaces of the precursor membrane after the infiltration or to conduct the polymerization in a state where a smooth film is press-contacted thereto, so that the polymerization is not conducted in a state where the polymerizable monomer having ion-exchange groups of the opposite polarity are thickly deposed on the uppermost surface of the precursor membrane.

In the second method, the crosslinking polymerizable composition is infiltrated into the voids in the porous film and is polymerized in quite the same manner as in the case of producing the precursor membrane in the above first production method with the exception of using a crosslinking polymerization composition that contains, as polymerizable monomers, a polymerizable monomer having ion-exchange groups and a polymerizable monomer having functional groups capable of introducing the ion-exchange groups of a polarity opposite to that of the above ion-exchange groups.

The polymerizable monomer having ion-exchange groups and the polymerizable monomer having functional groups capable of introducing the ion-exchange groups of a polarity opposite to the above ion-exchange groups, may be blended at a ratio that is suitably determined depending upon the ratio of the anion-exchange groups and the cation-exchange groups in the ion-exchange membrane that is to be obtained. As described already, it is desired that the amount of the ion-exchange groups excessively existing is about 1.01 to about 10 times, preferably, about 1.05 to about 5 times and, more preferably, about 1.1 to about 3 times as great as the amount of the other ion-exchange groups.

There is no particular limitation on the method of introducing the other ion-exchange groups after the polymerization in the second method or the first method, and the ion-exchange groups may be introduced in compliance with a known method of producing ion-exchange resins. That is, the cation-exchange groups can be introduced by conducting the treatment such as sulfonation, chlorosulfonation, phosphonium-imparting treatment or hydrolysis. As for the aromatic hydrocarbon rings, for example, the sulfonic acid groups (cation-exchange groups) can be easily introduced by the treatment with a sulfonating agent such as concentrated sulfuric acid, fumed sulfuric acid, sulfur trioxide or chlorosulfonic acid. Further, the anion-exchange groups can be introduced by the treatment such as amination or alkylation. Functional groups such as primary to tertiary amino groups form quaternary ammonium groups (anion-exchange groups) with the halogenated alkyl and, similarly, the functional groups such as halogenated alkyl groups form quaternary ammonium groups with primary to tertiary amines.

So far as the predetermined ratio of amounts is satisfied, the ion-exchange groups excessively existing can be introduced by using the polymerizable monomer having the ion-exchange groups or can be introduced by using the polymerizable monomer having functional groups capable of introducing the above ion-exchange groups.

In the present invention, the dipolar ion-exchange membrane obtained as described above is washed to remove unpolymerized monomers, and is used as the ion-exchange membrane 6 for the working electrode assembly 1.

By using a cell divided into two chambers with the thus obtained ion-exchange membrane as a partitioning wall, the membrane resistance of the ion-exchange membrane (dipolar ion-exchange membrane) is found as a difference between a resistance across the electrodes and a resistance across the electrodes of when no ion-exchange membrane is installed by measuring the resistance across the electrodes at 25° C. by using an AC bridge (frequency of 1000 cycles/second) in a state where the cell is filled with a 3 mols/L sulfuric acid aqueous solution. Similarly, by using the cell divided into two chambers with the ion-exchange membrane as a partitioning wall, the medicine permeation factor is measured by measuring a medicine concentration in a chamber of a sodium chloride aqueous solution by introducing a medicine solution of a concentration that is used into one chamber and introducing a 0.1 mol/L sodium chloride aqueous solution into another chamber, and flowing a current at a density of 0.5 mA/cm$^2$ for one hour at 25° C.

-Ion-Exchange Membrane 8-

In the present invention, the ion-exchange membrane 8 which is so arranged as to face the living body interface (skin) 7 to where the medicine is to be administered, is capable of permeating the medicine. When a cationic medicine is to be used, there is used a cation-exchange membrane which permits the cations to pass through. When an anionic medicine is to be used, there is used an anion-exchange membrane which permits the anions to pass through. As such ion-exchange membranes, there can be used known ion-exchange membranes. From the standpoint of an excellent mechanical strength, however, there can be, preferably, used an ion-exchange membrane with a crosslinking ion-exchange resin filled in the porous film like the one described above. Here, however, the ionic polarity is just opposite to that of the above-mentioned ion-exchange membrane 6.

Besides, the ion-exchange membrane 8 may be not the above mentioned dipolar ion-exchange membrane.

(Counter Electrode Assembly 2)

In the iontophoresis device shown in FIG. 1, the counter electrode assembly 2 has an electrode (counter electrode) 4' that faces the working electrode 4 of the working electrode assembly 1 and can assume, without any limitation, a structure used for a portion including an electrode that becomes a counter electrode in an ordinary iontophoresis device. That is, the counter electrode assembly 2 may be the electrode (counter electrode 4') itself, may be an assembly in which the electrode (counter electrode 4') is arranged on a sheet of an ionically conducting gel, a porous film or a woven fabric, or may be an assembly in which the electrode (counter electrode 4') is arranged on an ion-exchange membrane using a porous film as the reinforcement or on any other ion-exchange membrane. Preferably as shown in FIG. 1, the counter electrode 4', an electrolyte-containing portion 9 containing an ionic electrolyte and an ion-exchange membrane 10 are laminated in this order, the ion-exchange membrane 10 being arranged on the living body interface. In this case, the ion-exchange membrane 10 may be the one that has heretofore been known. Preferably, however, the ion-exchange membrane 10 is the one obtained by filling the porous film with the ion-exchange resin like the one described above from the standpoint of excellent mechanical strength. Further, the ion-exchange membrane 10 may be the one which selectively permits the permeation of ions of a polarity same as, or opposite to, that of the pharmacological ions of the desired medicine. Preferably, however, the ion-exchange membrane 10 is the one that selectively permeates ions of the polarity opposite to that of the pharmacological ions of the desired medicine to prevent the permeation of the desired medicine into the counter electrode assembly from the living body.

The electrolyte-containing portion 9 in the counter electrode assembly 2 may be a solution itself obtained by dissolving an ionic electrolyte in a solvent such as water or an ethanol, a gel obtained by mixing the above solution with a polyvinyl alcohol or a polyvinyl pyrrolidone, or the one obtained by impregnating a porous film or a gauze with the above solution. There can be used any ionic electrolyte not having poisonous character without limitation, such as sodium chloride or potassium chloride, if it dissolves in a solvent such as water or ethanol and exhibits ionic property.

Further, like in the case of the working electrode assembly 1, the counter electrode assembly 2 may be provided with an ion-exchange membrane between the counter electrode 4' and the ion-exchange membrane 10, may be provided with a sheet capable of permeating ions comprising an ionically conducting gel, a porous film or a woven fabric between the ion-exchange membrane 10 and the living body interface, or may be provided with an ionically conducting gel or an ionically electrolytic solution or with a porous film or a woven fabric impregnated with the ionically electrolytic solution between the counter electrode 4, and the ion-exchange membrane closest thereto.

(Power Source Unit 3)

As the power source unit 3 in the iontophoresis device, there can be used any power source unit that is used in an ordinary iontophoresis device without limitation. When the working electrode assembly 1, counter electrode assembly 2 and the power source unit 3 are independent from each other, there can be used an external power source that can be connected to a battery or to a power source of the system. In such a case, it is desired to use in combination a power source control system such as a system for stabilizing the voltage or the current or a system for applying a pulse current. When the working electrode assembly 1, counter electrode assembly 2 and power source unit 3 are used being incorporated in a backing material, a cell can be used as the power source portion. The cell may be a coin type silver oxide cell, an air-zinc cell or a lithium ion cell.

EXAMPLES

The invention will be described more concretely by way of the following Examples and Comparative Examples to which only, however, the invention is in no way limited. Properties of the ion-exchange membranes shown in Examples and Comparative Examples were measured by the methods described below.

(1) Ion-Exchange Capacity and Water Content:

The ion-exchange membrane was immersed in a 1 (mol/L) HCl aqueous solution for not less than 10 hours.

Thereafter, in the case of the cation-exchange membrane, the proton type was changed to the sodium ion type with a 1 (mol/L) NaCl aqueous solution, and the protons were determined with a sodium hydroxide aqueous solution by using a potential-difference titration device (COMTITE-900, manufactured by Hiranuma Sangyo Co.)(A mols). In the case of the anion-exchange membrane, on the other hand, a chloride ion type was changed to a nitric acid ion type by using a 1 mol/L $NaNO_3$ aqueous solution, and the liberated chloride ions were determined with a silver nitrate aqueous solution by using the potential-difference titration device (COMTITE-900, manufactured by Hiranuma Sangyo Co.)(A mols).

Next, the same ion-exchange membrane was immersed in a 1 mol/L HCl aqueous solution for not less than 4 hours, and was washed with the ion-exchanged water to a sufficient degree. The membrane was taken out, water on the surfaces thereof was wiped with a tissue paper or the like, and the weight (W g) thereof when wet was measured.

Next, the membrane was dried at 60° C. for 5 hours under a reduced pressure, and the weight was measured (D g).

Based on the above measured values, the ion-exchange capacity was found in compliance with the following formula, Ion-exchange capacity=$A \times 1000/W$ [mmol/g-dry weight] Water content=$100 \times (W-D)/D$[%]

(2) Amount of Cation-Exchange Groups and Amount of Anion-Exchange Groups.

The ion-exchange membrane was immersed in a 1 mol/L HCl aqueous solution for not less than 10 hours, washed with the ion-exchanged water to a sufficient degree, and was dried at 60° C. for 5 hours under a reduced pressure. The obtained ion-exchange membrane was put to the elemental analysis, the amount of the cation-exchange groups was calculated from the content of S and the amount of the anion-exchange groups was calculated from the content of N.

(3) Membrane Resistance.

An ion-exchange membrane was held in a two-chamber cell equipped with a platinum black electrode, a 3 mol/L sulfuric acid aqueous solution was filled on both sides of the ion-exchange membrane, a resistance across the electrodes was measured relying on an AC bridge (frequency of 1000 cycles/sec) at 25° C., and the membrane resistance was found relying upon a difference between the resistance across the electrodes and the resistance across the electrodes of when the ion-exchange membrane was not set up. The membrane used for the measurement had been equilibrated in advance in a 3 mol/L sulfuric acid aqueous solution.

(4) Amounts of Medicine Permeation and Voltages Applied to the Cell.

Figure 2:
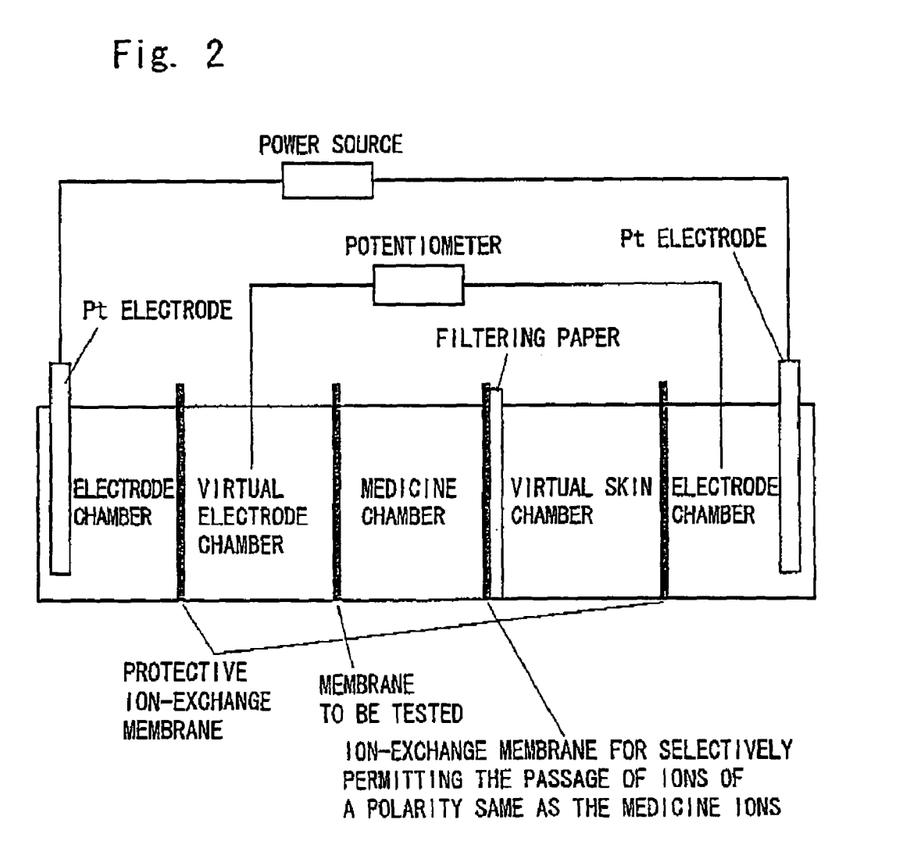
FIG. 2 is a view schematically illustrating a device used for measuring the amounts of administration of the medicine in Examples.

An ion-exchange membrane to be measured, an ion-exchange membrane for selectively permeating ions of the same sign as the medicine, and protective ion-exchange membranes for preventing the medicine from arriving at the electrode were set in a cell shown in FIG. 2. A medicine solution chamber was filled with an aqueous solution of medicine of a predetermined concentration. A virtual electrode chamber, a virtual skin chamber and two electrode chambers were filled with a 0.1 mol/L sodium chloride aqueous solution. As the ion-exchange membrane for selectively permeating the ions of the same polarity as the medicine, there was used an anion-exchange membrane obtained in the following Preparation Example A. As the protective ion-exchange membrane, there was used a cation-exchange membrane obtained in Preparation Example B.

Next, an electric current was supplied for one hour at a predetermined constant current density at 25° C. and stirring the medicine solution chamber and the virtual electrode chamber. After the supply of electric current has been terminated, the solution in the virtual electrode chamber was readily drained and the amount of medicine was measured relying on a liquid chromatography. As a detector, there was used a UV detector.

In this case, the lower limit of detection was about 0.00001 $\mu$mol/cm$^2$ for all of ascorbic acid phosphate, dexamethasone phosphate and adenosine triphosphate.

Further, a voltage applied to the cell was measured by using a potentiometer shown in FIG. 2.

Preparation Example A

Preparation of the Ion-Exchange Membrane for Selectively Permeating the Medicine Ions (Anion-Exchange Membrane)

There was prepared a crosslinking polymerizable composition comprising 380 g of a chloromethylstyrene, 20 g of a divinylbenzene and 20 g of a t-butylperoxyethyl hexanoate. 420 Grams of this crosslinking polymerizable composition was introduced into a 500-ml glass container and in which a porous film (made of a polyethylene having a weight average molecular weight of 250,000, a thickness of 25 $\mu$m, an average pore size of 0.03 $\mu$m, percentage of voids of 37%) measuring 20 cm×20 cm was immersed under the atmospheric pressure at 25° C. for 10 minutes, so that the porous film was impregnated with the crosslinking polymerizable composition.

Next, the porous film was taken out from the crosslinking polymerizable composition, covered on its both sides with polyester films of 100 $\mu$m thick, and was heated and polymerized under a nitrogen pressure of 3 kg/cm$^2$ at 80° C. for 5 hours.

Thereafter, the obtained membrane was reacted in an aminating bath comprising 10 parts by weight of 30% by weight of a trimethylamine, 5 parts by weight of water and 5 parts by weight of acetone at room temperature for 5 hours to obtain a quaternary ammonium type anion-exchange membrane.

Preparation Example B

Preparation of Protective Ion-Exchange Membrane (Cation-Exchange Membranes)

There was used the crosslinking polymerizable composition which contains 90 parts by weight of styrene, 10 parts by weight of divinylbenzene and 5 parts by weight of t-butylperoxyethyl hexanoate and with which the porous film was impregnated in the same manner as in Preparation Example A. The porous films were taken out from the crosslinking polymerizable compositions, covered on their both sides with polyester films of 100 $\mu$m thick, and were heated and polymerized under a nitrogen pressure of 3 kg/cm$^2$ at 80° C. for 5 hours. Thereafter, the obtained membranes were immersed in a mixture of concentrated sulfuric acid of 98% and a chlorosulfonic acid of a purity of not lower than 90% at a ratio of 1:1 at 40° C. for 45 minutes to obtain sulfonic acid type cation-exchange membranes.

Preparation Example 1

Preparation of a Dipolar Cation-Exchange Membrane

400 Grams of a styrene, 12 g of a divinylbenzene and 20 g of a t-butylperoxyethyl hexanoate were mixed together. 400 Grams of the obtained monomer composition was introduced into a 500-ml glass container and in which a porous film (made of a polyethylene having a weight average molecular weight of 250,000, a thickness of 25 $\mu$m, an average pore size of 0.03 $\mu$m, percentage of voids of 37%, a size of 20 cm×20 cm) was immersed.

Next, the porous film was taken out from the monomer composition, covered on its both sides with a polyester film of 100 $\mu$m thick, and was heated and polymerized under a nitrogen pressure of 3 kg/cm$^2$ at 80° C. for 5 hours.

The obtained membrane was immersed in a mixture of concentrated sulfuric acid of 98% and a chlorosulfonic acid of a purity of not lower than 90% at a ratio of 1:1 at 40° C. for 60 minutes to obtain a cation-exchange membrane (precursor membrane) A having a crosslinking structure.

Next, the cation-exchange membrane A was dried at room temperature for 24 hours, and was immersed in a liquid containing polymerizable monomers having ion-exchange groups shown in Table 1 at room temperature for 30 minutes.

Next, the ion-exchange membrane was taken out from the monomer composition, covered on its both sides with a polyester film of 100 $\mu$m thick as a peeling member, and was heated and polymerized under a nitrogen pressure of 3 kg/cm$^2$ at 80° C. for 5 hours. The obtained polymer was immersed in methanol for 2 hours to obtain a dipolar cation-exchange membrane (ion-exchange membrane (1)) to be used for the working electrode assembly 1. The ion-exchange membrane was measured for its cation-exchange capacity, amount of cation-exchange groups, amount of anion-exchange groups, water content, membrane resistance and membrane thickness. The results were as shown in Table 1.

Preparation Examples 2 to 4

Preparation of Dipolar Cation-Exchange Membranes

The cation-exchange membranes A prepared above were dried at room temperature for 24 hours, and were immersed in a liquid containing polymerizable monomers having ion-exchange groups shown in Table 6 at room temperature for 30 minutes.

Next, the ion-exchange membranes were taken out from the monomer composition, covered on their both sides with a polyester film of 100 $\mu$m thick as a peeling member, and were heated and polymerized under a nitrogen pressure of 3 kg/cm² at 80° C. for 5 hours. The obtained polymers were immersed in methanol for 2 hours to obtain dipolar cartion-exchange membranes (ion-exchange membranes (2) to (4)). Table 6 shows cation-exchange capacities, amounts of cation-exchange groups, amounts of anion-exchange groups, water contents, membrane resistances and membrane thicknesses of these ion-exchange membranes.

Table 1 also shows the characteristics of the Neosepta CMX which is a cation-exchange membrane placed in the market.

porous membranes (made of a polyethylene having a weight average molecular weight of 250,000, a thickness of 25 μm, an average pore size of 0.03 μm, percentage of voids of 37%, a size of 20 cm×20 cm) were immersed.

Next, the porous membranes were taken out from the monomer compositions, covered on their both sides with a polyester film of 100 μm thick, and were heated and polymerized under a nitrogen pressure of 3 kg/cm² at 80° C. for 5 hours.

TABLE 1

| prep. Ex | Ion-exchange membrane | Composition of polymerizable monomer (wt. pts.) | | | | Characteristic of ion-exchange membrane | | | | | |
|---|---|---|---|---|---|---|---|---|---|---|---|
| | | 4VP | DVB | PO | Toluene | Amount of cation-exchange groups [mmol/g of dry membrane] | Amount of anion-exchange groups [mmol/g of dry membrane] | Cation-exchange capacity [mmol/g of dry membrane] | Water content [%] | Membrane resistance [Ω·cm²] | Membrane thickness [μm] |
| — | Cation-exchange membrane A | — | — | — | — | 2.6 | 0 | 2.6 | 28 | 0.12 | 30 |
| 1 | Ion-exchange membrane (1) | 100 | 0 | 5 | 0 | 2.4 | 1.0 | 1.54 | 26 | 0.23 | 30 |
| 2 | Ion-exchange membrane (2) | 100 | 3 | 5 | 0 | 2.4 | 1.5 | 1.04 | 22 | 0.32 | 31 |
| 3 | Ion-exchange membrane (3) | 100 | 12 | 5 | 0 | 2.4 | 1.8 | 0.69 | 16 | 0.42 | 32 |
| 4 | Ion-exchange membrane (4) | 100 | 3 | 5 | 300 | 2.4 | 2.0 | 0.45 | 20 | 0.32 | 32 |
| | Neocepta CMX | | | | | 1.6 | 0 | 1.6 | 28 | 0.36 | 160 |

St: styrene
4VP: 4-vinylpyridine
DVB: divinylbenzene
PO: t-butylperoxyethyl hexanoate Preparation Examples 5 to 8

Preparation of Dipolar Cation-Exchange Membranes

Monomer compositions were obtained by mixing various monomers according to compositions shown in Table 2. The obtained monomer compositions each in an amount of 400 g were introduced into a 500-ml glass container and in which The obtained membranes were immersed in a mixture of concentrated sulfuric acid of 98% and a chlorosulfonic acid of a purity of not lower than 90% at a ratio of 1:1 at 40° C. for 60 minutes to obtain dipolar cation-exchange membranes (ion-exchange membranes (5) to (8)). Table 2 shows the cation-exchange capacities, amounts of cation-exchange groups, amounts of anion-exchange groups, water contents, membrane resistances and membrane thicknesses of these ion-exchange membranes.

TABLE 2

| prep. Ex. | Ion-exchange membrane | Composition of polymerizable monomer (wt. pts.) | | | | Characteristic of ion-exchange membrane | | | | | |
|---|---|---|---|---|---|---|---|---|---|---|---|
| | | St | 4VP | DVB | PO | Amount of cation-exchange groups [mmol/g of dry membrane] | Amount of anion-exchange groups [mmol/g of dry membrane] | Cation-exchange capacity [mmol/g of dry membrane] | Water content [%] | Membrane resistance [Ω·cm²] | Membrane thickness [μm] |
| 5 | Ion-exchange membrane (5) | 55 | 45 | 5 | 5 | 1.6 | 1.2 | 0.45 | 29 | 0.13 | 30 |
| 6 | Ion-exchange membrane (6) | 55 | 45 | 10 | 5 | 1.6 | 1.2 | 0.63 | 25 | 0.16 | 29 |
| 7 | Ion-exchange membrane (7) | 55 | 45 | 15 | 5 | 1.5 | 1.1 | 0.91 | 23 | 0.32 | 28 |
| 8 | Ion-exchange membrane (8) | 77 | 23 | 5 | 5 | 1.9 | 0.6 | 1.4 | 33 | 0.09 | 31 |

St: styrene
4VP: 4-vinylpyridine
DVB: divinylbenzene
PO: t-butylperoxyethyl hexanoate

Examples 1 to 8

Amounts of permeation of the medicine were measured by using the dipolar cation-exchange membranes prepared in Preparation Examples 1 to 8 as membranes to be tested and a 10 mmol/L solution of an ascorbic acid phosphate magnesium salt which is an anionic medicine at a current density of 0.5 mA/cm$^2$, and voltages applied to the cell were measured. Table 3 shows the ion-exchange membranes that were used, measured results of the amounts of permeation of the medicines and voltages.

Comparative Example 1

The amount of permeation of the medicine and the voltage applied to the cell were measured in the same manner as in Example 16 but using the Neosepta CMX which is a cation-exchange membrane (membrane properties are shown in Table 1). The results were as shown in Table 3.

Comparative Example 2

The amount of permeation of the medicine and the voltage applied to the cell were measured in the same manner as in Example 1 but using the cation-exchange membrane A (precursor membrane) that was prepared in preparing the dipolar cation-exchange membrane in Preparation Example 1. The results were as shown in Table 3.

TABLE 3

| | Ion-exchange membrane to be tested | Amount of permeation [μmol/cm$^2$] | Voltage [V] |
|---|---|---|---|
| Example 1 | Ion-exchange membrane (1) | Not detected | 10 |
| Example 2 | Ion-exchange membrane (2) | Not detected | 11 |
| Example 3 | Ion-exchange membrane (3) | Not detected | 11 |
| Example 4 | Ion-exchange membrane (4) | Not detected | 10 |
| Example 5 | Ion-exchange membrane (5) | Not detected | 9 |
| Example 6 | Ion-exchange membrane (6) | Not detected | 9 |
| Example 7 | Ion-exchange membrane (7) | Not detected | 11 |
| Example 8 | Ion-exchange membrane (8) | Not detected | 9 |
| Comparative Example 1 | Neosepta CMX | 0.00025 | 95 |
| Comparative Example 2 | Cation-exchange membrane A | 0.00028 | 10 |

Examples 9 and 10

Amounts of permeation of the medicines were measured in the same manner as in Example 1 but using the dipolar cation-exchange membrane (ion-exchange membrane (1)) prepared in Preparation Example 1 as a membrane to be tested and a 10 mmol/L solution of anionic medicines shown in Table 4 instead of the 10 mmols/L solution of the ascorbic acid phosphate magnesium salt at a current density of 0.5 mA/cm$^2$, and voltages applied to the cell were measured, too. The results were as shown in Table 4.

Comparative Examples 3 and 4

Amounts of permeation of the medicines were measured in the same manner as in Example 9 or Example 10 but using the Neosepta CMX which is the cation-exchange membrane (membrane properties are shown in Table 1) as a membrane to be tested, and voltages applied to the cell were measured, too. The results were as shown in Table 4.

Comparative Examples 5 and 6

The amounts of permeation of the medicines and the voltages applied to the cell were measured in the same manner as in Example 9 or Example 10 but using the cation-exchange membrane A (precursor membrane) that was prepared in preparing the dipolar cation-exchange membrane in Preparation Example 1. The results were as shown in Table 4.

TABLE 4

| | Ion-exchange membrane to be tested | Medicine | Amount of permeation [μmol/cm$^2$] | Voltage [V] |
|---|---|---|---|---|
| Example 9 | Ion-exchange membrane (1) | Dexamethasone phosphate disodium salt | Not detected | 12 |
| Example 10 | Ion-exchange membrane (1) | Adenosine triphosphate disodium salt | Not detected | 10 |
| Comparative Example 3 | Neosepta CMX | Dexamethasone phosphate disodium salt | 0.00014 | 80 |
| Comparative Example 4 | Neosepta CMX | Adenosine triphosphate disodium salt | 0.00018 | 75 |
| Comparative Example 5 | Cation-exchange membrane A | Dexamethasone phosphate disodium salt | 0.00015 | 12 |
| Comparative Example 6 | Cation-exchange membrane A | Adenosine triphosphate disodium salt | 0.00018 | 10 |

The invention claimed is:

1. An iontophoresis working electrode assembly comprising:
   a working electrode,
   a medicine containing portion containing an ionic medicine, and
   a dipolar ion-exchange membrane arranged between said working electrode and said medicine-containing portion,
   wherein the dipolar ion-exchange membrane comprises a porous film having voids thereon,
   wherein the voids in the porous film comprise a crosslinking ion-exchange resin into the which have been introduced both anion-exchange groups and cation-exchange groups,
   wherein the anion-exchange groups are present in an excess amount compared to the cation-exchange groups, or wherein the cation-exchange groups are present in an excess amount compared to the anion-exchange groups, and
   wherein said dipolar ion exchange membrane contains either the anion-exchange groups or the cation-exchange groups in an amount of 1.01 to 10 times as large as the amount of the other ion-exchange groups.

2. The iontophoresis working electrode assembly according to claim 1, wherein said dipolar ion-exchange membrane has a membrane resistance of not larger than 0.45 Ω·cm2 in a 3 mol/L sulfuric acid aqueous solution, and a permeation factor for said ionic medicine of not larger than 0.001μmol/hr·cm2 as measured at a current density of 0.5 mA/cm2.

3. An iontophoresis device, comprising:
   the iontophoresis working electrode assembly according to claim 1,
   a counter electrode assembly having a counter electrode facing said working electrode, and a power source unit electrically connected to said working electrode assembly and to said counter electrode assembly, wherein when said device is activated, electrophoresis of an ionic medicine contained in the medicine-containing portion of said working electrode assembly is achieved.

4. An iontophoresis working electrode assembly comprising:
- a working electrode,
- a medicine-containing portion containing an ionic medicine, and
- a dipolar ion-exchange membrane arranged between said working electrode and said medicine-containing portion, wherein the dipolar ion-exchange membrane comprises a porous film having voids thereon, wherein the voids in the porous film comprise a crosslinking ion-exchange resin into the which have been introduced both anion-exchange groups and cation-ion exchange groups, and wherein the anion-exchange groups in the cross-linking ion-exchange resin are present in an excess amount compared to the cation-exchange groups, or wherein the cation-exchange groups are present in an excess amount compared to the anion-exchange groups.

\* \* \* \* \*